United States Patent
Suzuki et al.

(10) Patent No.: US 11,639,338 B1
(45) Date of Patent: May 2, 2023

(54) COMPOUND PRODUCING METHOD, AND COMPOUND

(71) Applicant: Kureha Corporation, Tokyo (JP)

(72) Inventors: Shigeru Suzuki, Tokyo (JP); Nobuyuki Kusano, Tokyo (JP); Hisataka Kobayashi, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 17/905,799

(22) PCT Filed: Mar. 9, 2021

(86) PCT No.: PCT/JP2021/009099
§ 371 (c)(1),
(2) Date: Sep. 7, 2022

(87) PCT Pub. No.: WO2021/182422
PCT Pub. Date: Sep. 16, 2021

(30) Foreign Application Priority Data

Mar. 9, 2020 (JP) .............................. JP2020-039599

(51) Int. Cl.
*C07D 303/48* (2006.01)
*C07D 301/24* (2006.01)

(52) U.S. Cl.
CPC ......... *C07D 303/48* (2013.01); *C07D 301/24* (2013.01)

(58) Field of Classification Search
CPC ............................ C07D 303/48; C07D 301/24
See application file for complete search history.

(56) References Cited

U.S. PATENT DOCUMENTS

| | | |
|---|---|---|
| 10,945,434 B2 | 3/2021 | Harigae et al. |
| 2020/0288714 A1* | 9/2020 | Harigae ............... A01N 43/653 |

FOREIGN PATENT DOCUMENTS

| | | | |
|---|---|---|---|
| WO | 2019/093522 A1 | 5/2019 | |
| WO | WO-2019093522 A1 * | 5/2019 | ........... A01N 43/653 |

OTHER PUBLICATIONS

Scott et al. J. Heterocyclic Chem. 1984, 21, 903-904 (Year: 1984).*
Hummelen et al. Tetrahedron Lett. 1978, 12, 1089-1092 (Year: 1978).*
Nanjo, K. et al., "Enantioface-Differentiating Epoxidation of Alkylidenemalononitriles with Molecular Oxygen, catalyzed by Chiral Tertiary Amines", Chemical & Pharmaceutical Bulletin, 1981, 29 (2), pp. 336-343 p. 338, p. 342, column "Preparation of IVa-b".
Hurtaud, D. et al., "Synthesis and Characterization of Stable 2-Cyano-2-Carboximic Acid Alkyl Ester-Oxiranes and 2,2-Dicarboximidic Acid Dialkyl Ester-Oxiranes", Tetrahedron Letters, 1999, 40(27), pp. 5001-5004 p. 5003, scheme 3, compound 1 —> compound 6.
Harrison, J. M. et al., "A novel rearrangement of the adduct from CS-epoxide and dioxan-2-hydroperoxide", Tetrahedron Letters, 1981, 22(7), pp. 679-682 pp. 679, 681, compound 2—compound 4.
Scott, J. H. et al., "Reactions of Substituted Phenacyl Bromides with Various Bases, o- and p-Nitrophenacyl Bromide. I", Journal of Heterocyclic Chemistry, 1984, 21 (3), pp. 903-904 p. 903, compound 1 + KCN—compound 4, p. 904, left column.
Svoboda, J. et al., "Reaction of 4-substituted benzaldehydes and acetophenones with chloroacetonitrile", Collection of Czechoslovak Chemical Communications, 1988, 53(4), pp. 822-832 entire text.
Muller, A. J. et al., "Reductive Condensation of Methyl Arylglyoxylates. Direct Synthesis of 2,3-Bis(carbomethoxy) stilbene Oxides and Related Systems", Journal of Organic Chemistry, 1982, 47(12), pp. 2342-2352 entire text.
Database Registry [Online] Retrieved from STN, Entered STN: Dec. 20, 2007, [retrieval date Apr. 5, 2021], CAS Registry No. 959055-76-6 entire text.
Written Opinion of the International Searching Authority Regarding International Application No. PCT/JP2021/009099, dated May 18, 2021.
Office Action for CN Application No. 202180014854.3, dated Dec. 5, 2022, 6 pages.
English translation of Office Action for CN Application No. 202180014854.3, dated Dec. 5, 2022, 7 pages.

\* cited by examiner

*Primary Examiner* — Matthew P Coughlin
(74) *Attorney, Agent, or Firm* — Abel Schillinger, LLP

(57) ABSTRACT

A method by which an intermediate product of an azole derivative can be produced at a lower cost and in a higher yield than those of known production methods is realized. A method of producing a compound of General Formula (III) includes: producing the compound of General Formula (III) by allowing a cyanide compound to act on a ketone derivative of General Formula (II); and washing the compound of General Formula (III) produced in the producing the compound of General Formula (III) with an alkaline aqueous solution.

2 Claims, No Drawings

COMPOUND PRODUCING METHOD, AND COMPOUND

TECHNICAL FIELD

The present invention relates to a method of producing a compound, and a novel compound.

BACKGROUND ART

An azole derivative is useful as an agricultural or horticultural chemical exhibiting a high controlling effect. To produce an azole derivative, a method of producing an intermediate compound of an azole derivative has been studied. For example, Patent Document 1 describes a method of producing methyl-2-(2-chloro-4-(2,4-dichlorophenoxy)phenyl)-2-oxoacetate, which is an intermediate product of an azole derivative.

Furthermore, Non-Patent Document 1 describes a reaction that converts an α-haloketone group into a cyanooxirane group, and Non-Patent Document 2 describes a reaction that converts a cyano group into an ester group.

CITATION LIST

Patent Document

Patent Document 1: WO 2019/093522 (Publication Date: May 16, 2019)

Non-Patent Literature

Non-Patent Document 1: James H. et al., Journal of Heterocyclic Chemistry, 21(3), 903-4; 1984
Non-Patent Document 2: Muller A. J. et al., Journal of Organic Chemistry, 47, 2342-2352; 1982

SUMMARY OF INVENTION

Technical Problem

In the method of producing an intermediate product of an azole derivative described in Patent Document 1, a ketone group is substituted by a ketoester group using iodine or iodomethane. However, since iodine and iodomethane are expensive, there is a problem of increased production cost of an intermediate product of an azole derivative. Furthermore, yields in production methods described in Patent Document 1 and Non-Patent Documents 1 and 2 are low. Therefore, a method of producing an intermediate product of an azole derivative in a higher yield is demanded.

The present invention has been completed in light of the problems described above, and an object of an aspect of the present invention is to realize a method by which an intermediate product of an azole derivative can be produced at a lower cost and in a higher yield than those of known production methods.

Solution to Problem

To solve the problems described above, the production method according to one aspect of the present invention is a method of producing a compound represented by General Formula (III),

[Chem. 1]

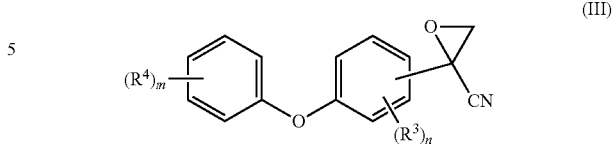

where $R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;
m is an integer from 0 to 5, and when m is 2 or greater, a plurality of $R^4$ moieties may be different from each other; and
n is an integer from 0 to 4, and when n is 2 or greater, a plurality of $R^3$ moieties may be different from each other;
the method comprising:
producing the compound represented by General Formula (III) above by allowing a cyanide compound to act on a ketone derivative represented by General Formula (II), and washing the compound represented by General Formula (III) above produced in the producing the compound represented by General Formula (III) above with an alkaline aqueous solution;

[Chem. 2]

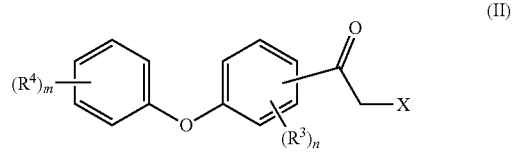

where X is a halogen atom, and
$R^3$, $R^4$, m, and n in Formula (II) are respectively identical to $R^3$, $R^4$, m, and n in Formula (III) above.

To solve the problems described above, the production method according to one aspect of the present invention is a method of producing a compound represented by General Formula (IV)

[Chem. 3]

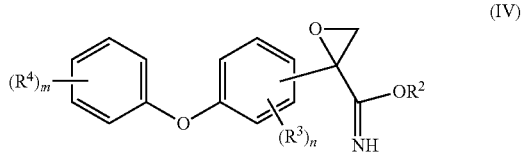

where $R^2$ is a $C_1$-$C_6$-alkyl group;
$R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;
m is an integer from 0 to 5, and when m is 2 or greater, a plurality of $R^4$ moieties may be different from each other; and
n is an integer from 0 to 4, and when n is 2 or greater, a plurality of $R^3$ moieties may be different from each other;
the method comprising:
producing the compound represented by General Formula (IV) above by allowing an alkoxide compound having from 1 to 6 carbons to act on a compound represented by General Formula (III),

[Chem. 4]

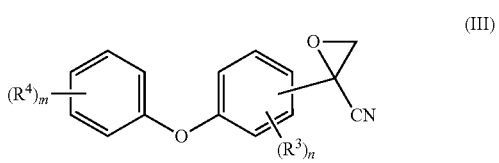

(III)

where $R^3$, $R^4$, m, and n in Formula (III) are respectively identical to $R^3$, $R^4$, m, and n in Formula (IV) above.

To solve the problems described above, the production method according to one aspect of the present invention is a method of producing a compound represented by General Formula (V),

[Chem. 5]

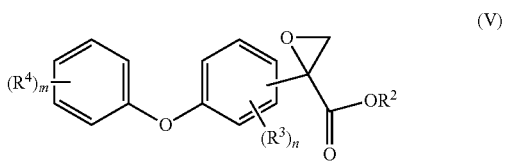

(V)

where $R^2$ is a $C_1$-$C_6$-alkyl group;

$R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;

m is an integer from 0 to 5, and when m is 2 or greater, a plurality of $R^4$ moieties may be different from each other; and n is an integer from 0 to 4, and when n is 2 or greater, a plurality of $R^3$ moieties may be different from each other;

the method comprising:

producing a compound represented by General Formula (IV) by allowing an alkoxide compound having from 1 to 6 carbons to act on a compound represented by General Formula (III), and producing the compound represented by General Formula (V) above by allowing an acidic compound to act on the compound represented by General Formula (IV) above produced in the producing the compound represented by General Formula (IV) above;

[Chem. 6]

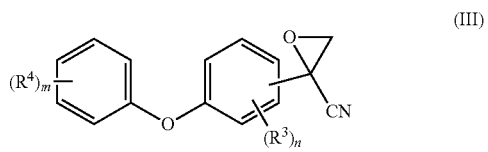

(III)

where $R^3$, $R^4$, m, and n in Formula (III) are respectively identical to $R^3$, $R^4$, m, and n in Formula (V) above; and

[Chem. 7]

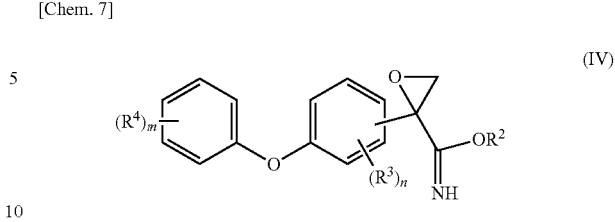

(IV)

where $R^2$, $R^3$, $R^4$, m, and n in Formula (IV) are respectively identical to $R^2$, $R^3$, $R^4$, m, and n in Formula (V).

To solve the problems described above, the production method according to one aspect of the present invention is a method of producing a compound represented by General Formula (V),

[Chem. 8]

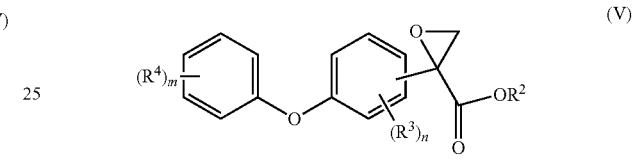

(V)

where $R^2$ is a $C_1$-$C_6$-alkyl group;

$R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;

m is an integer from 0 to 5, and when m is 2 or greater, a plurality of $R^4$ moieties may be different from each other; and n is an integer from 0 to 4, and when n is 2 or greater, a plurality of $R^3$ moieties may be different from each other;

the method comprising:

producing a compound represented by General Formula (III) by allowing a cyanide compound to act on a ketone derivative represented by General Formula (II), producing a compound represented by General Formula (IV) by allowing an alkoxide compound having from 1 to 6 carbons to act on a reaction solution after the producing a compound represented by General Formula (III) above; and producing the compound represented by General Formula (V) above by allowing an acidic compound to act on a reaction solution after the producing a compound represented by General Formula (IV) above;

[Chem. 9]

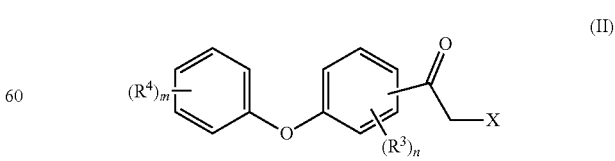

(II)

where X is a halogen atom, $R^3$, $R^4$, m, and n in Formula (II) are respectively identical to $R^3$, $R^4$, m, and n in Formula (V) above;

[Chem. 10]

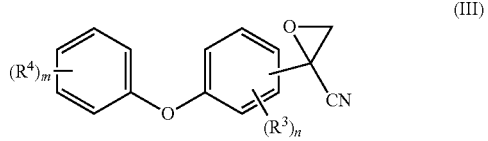

(III)

where $R^3$, $R^4$, m, and n in Formula (III) are respectively identical to $R^3$, $R^4$, m, and n in Formula (V) above; and

[Chem. 11]

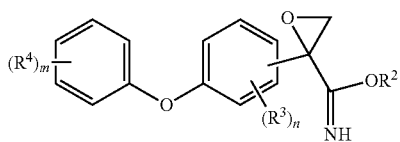

(IV)

where $R^2$, $R^3$, $R^4$, m, and n in Formula (IV) are respectively identical to $R^2$, $R^3$, $R^4$, m, and n in Formula (V) above.

To solve the problems described above, the compound according to one aspect of the present invention is a compound represented by General Formula (VI) below:

[Chem. 12]

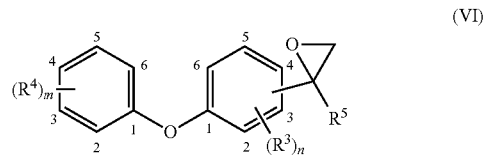

(VI)

where $R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;
m is an integer from 0 to 5, and when m is 2 or greater, a plurality of $R^4$ moieties may be different from each other;
n is an integer from 0 to 4, and when n is 2 or greater, a plurality of $R^3$ moieties may be different from each other;
$R^5$ is —CN or —CNHOR$^2$, and
$R^2$ is a $C_1$-$C_6$-alkyl group.

Advantageous Effects of Invention

According to one aspect of the present invention, an intermediate product of an azole derivative can be produced at a lower cost and in a higher yield than those of known production methods.

DESCRIPTION OF EMBODIMENTS

A preferred embodiment for carrying out the present invention will now be explained. Moreover, the embodiment explained below illustrates a single representative example of the present invention, and it should not be interpreted that the scope of the present invention is narrowed by this embodiment.

1. Method of Producing Compound Represented by General Formula (III)

The method of producing a compound represented by General Formula (III) according to one aspect of the present invention (hereinafter, referred to as "production method 1") will be described.

[Chem. 13]

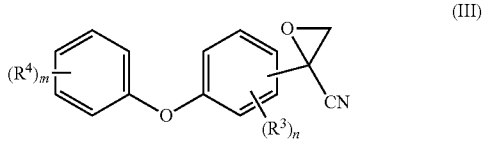

(III)

In Formula (III), $R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$ haloalkoxy group;
m is an integer from 0 to 5, and when m is 2 or greater, a plurality of $R^4$ moieties may be different from each other; and
n is an integer from 0 to 4, and when n is 2 or greater, a plurality of $R^3$ moieties may be different from each other.

The compound represented by General Formula (III) above is an intermediate product of an azole derivative represented by General Formula (I) below. For convenience of explanation, the azole derivative represented by General Formula (I) is referred to as "azole derivative (I)", and the compound represented by General Formula (III) is referred to as "intermediate product (III)".

[Chem. 14]

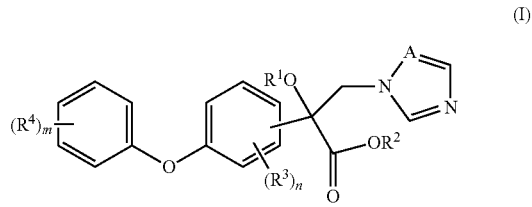

(I)

In Formula (I), A is N or CH;
$R^1$ and $R^2$ are each independently hydrogen or a $C_1$-$C_6$-alkyl group;
$R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;
m is an integer from 0 to 5, and when m is 2 or greater, a plurality of $R^4$ moieties may be different from each other; and
n is an integer from 0 to 4, and when n is 2 or greater, a plurality of $R^3$ moieties may be different from each other.

$R^3$, $R^4$, m, and n in General Formula (III) above are respectively identical to $R^3$, $R^4$, m, and n in Formula (I) above.

The $C_1$-$C_6$-alkyl group is a linear or branched alkyl group having from 1 to 6 carbon atoms, and examples thereof include a methyl group, an ethyl group, a 1-methylethyl group, a 1,1-dimethylethyl group, a propyl group, a 1-methylpropyl group, a 2-methylpropyl group, a 1,1-dimethylpropyl group, a 2,2-dimethylpropyl group, a 1-ethylpropyl group, a butyl group, a 1-methylbutyl group, a 2-methylbutyl group, a 3-methylbutyl group, a 3,3-dimethylbutyl group, a 2,2-dimethylbutyl group, a 1,1-dimethylbutyl group, a 1-ethylbutyl group, a 2-ethylbutyl group, a pentyl group, a 1-methylpentyl group, a 2-methylpentyl group, a 3-methylpentyl group, and a 4-methylpentyl group.

The $C_1$-$C_6$-haloalkyl group has one or more halogen atoms as substituents at substitutable positions of the $C_1$-$C_6$-alkyl group described above, and in a case of substitution with two or more halogen groups, the halogen groups may be the same or different. Examples of the halogen group include chlorine, bromine, iodine, and fluorine groups. Specific examples include chloromethyl, 2-chloroethyl, 2,3-dichloropropyl, bromomethyl, chlorodifluoromethyl, trifluoromethyl, and 3,3,3-trifluoropropyl groups.

The $C_1$-$C_6$-alkoxy group is a linear or branched alkoxy group having from 1 to 6 carbon atoms, and examples thereof include a methoxy group, an ethoxy group, a propoxy group, a 1-methylethoxy group, a 1-methylpropoxy group, a 2-methylpropoxy group, a 1-ethylpropoxy group, a butoxy group, a 1,1-dimethylethoxy group, a 2-methylbutoxy group, a 3,3-dimethylbutoxy group, a 2,2-dimethylbutoxy group, a 1,1-dimethylbutoxy group, a pentyloxy group, a 1-methylpentyloxy group, a 2,2-dimethylpropoxy group, a 1,1-dimethylpropoxy group, a 1-methylbutoxy group, a 3-methylbutoxy group, a 1-ethylbutoxy group, a 2-ethylbutoxy group, a 2-methylpentyloxy group, a 3-methylpentyloxy group, and a 4-methylpentyloxy group.

The $C_1$-$C_6$-haloalkoxy group has one or more halogen atoms as substituents at substitutable positions of the $C_1$-$C_6$-alkoxy group described above, and in a case of substitution with two or more halogen groups, the halogen groups may be the same or different. Examples of the halogen group include halogen groups exemplified for the description of the $C_1$-$C_6$-haloalkyl group above.

The production method 1 according to one aspect of the present invention includes: producing the compound represented by General Formula (III) above by allowing a cyanide compound to act on a ketone derivative represented by General Formula (II) (Step 1-1); and washing the compound represented by General Formula (III) above produced in the producing the compound represented by General Formula (III) above with an alkaline aqueous solution (Step 1-2).

[Chem. 15]

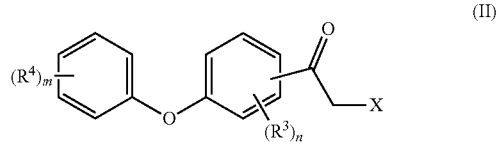

In Formula (II), X is a halogen atom, and $R^3$, $R^4$, m, and n are respectively identical to $R^3$, $R^4$, m, and n in Formula (III) above.

Examples of the halogen atom include a chlorine atom, a bromine atom, an iodine atom, and a fluorine atom.

In the production method 1 according to one aspect of the present invention, an intermediate product (III) is produced from a ketone derivative represented by General Formula (II) (hereinafter, referred to as "ketone derivative (II)") according to Scheme 1 below. Note that $R^3$, $R^4$, m, and n in the scheme below respectively correspond to $R^3$, $R^4$, m, and n in General Formula (III) above.

Scheme 1

[Chem. 16]

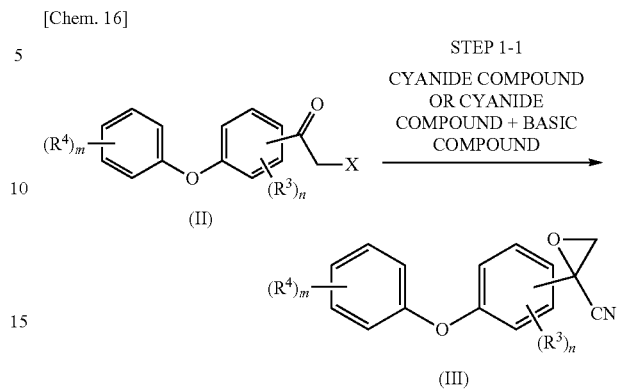

Step 1-1: Production of Intermediate Product (III)

In the production method 1 according to one aspect of the present invention, in Step 1-1, the intermediate product (III) is produced by allowing a cyanide compound to act on the ketone derivative (II) in an organic solvent. As the organic solvent, a solvent that allows progress of the reaction of Step 1-1 is chosen. Examples of such an organic solvent include methanol, ethanol, acetone, dimethylacetamide, toluene, and a mixed solvent of toluene and methanol. From the perspective of yield, methanol is preferably selected as the organic solvent. Step 1-1 can be performed at a reaction temperature of ice-cold or room temperature (20° C.). From the perspective of yield, Step 1-1 is preferably performed in an ice-cold condition, and is more preferably performed in methanol in an ice-cold condition.

Examples of the cyanide compound include potassium cyanide, sodium cyanide, and acetone cyanohydrin. From the perspective of yield, potassium cyanide is preferred.

In Step 1-1, the amount of the cyanide compound acting on the ketone derivative (II) is preferably 1 equivalent or greater with respect to 1 equivalent (eq.) of the ketone derivative (II) from the perspective of performing the reaction without excess or deficiency. Furthermore, from the perspective of yield, the amount of the cyanide compound acting on the ketone derivative (II) is preferably 3 equivalents or less with respect to 1 equivalent (eq.) of the ketone derivative (II). From the perspective of yield, the amount of the cyanide compound acting on the ketone derivative (II) is more preferably 1.2 equivalents or greater and 2 equivalents or less with respect to 1 equivalent (eq.) of the ketone derivative (II).

In one aspect of the present invention, in a case where potassium cyanide is selected as the cyanide compound in Step 1-1, the amount of potassium cyanide acting on the ketone derivative (II) is most preferably 1.3 equivalents (eq.) of potassium cyanide with respect to 1 equivalent (eq.) of the ketone derivative (II). Furthermore, in one aspect of the present invention, in a case where acetone cyanohydrin is selected as the cyanide compound in Step 1-1, the amount of acetone cyanohydrin acting on the ketone derivative (II) is most preferably 2 equivalents (eq.) of acetone cyanohydrin with respect to 1 equivalent (eq.) of the ketone derivative (II).

In a case where acetone cyanohydrin is selected as the cyanide compound, from the perspective of progress of the reaction, Step 1-1 needs to be performed in coexistence with a basic compound. Examples of the basic compound include potassium carbonate, N-ethyldiisopropylamine (DIPEA), potassium hydroxide, potassium hydrogen carbonate, and sodium hydrogen carbonate. From the perspective of yield, potassium carbonate or N-ethyldiisopropylamine (DIPEA) is preferred. Note that, in a case where the cyanide compound is potassium cyanide or sodium cyanide, since these compounds correspond to bases in a broad sense and the base and the cyanide coexist, the reaction progresses without coexistence of another basic compound.

The amount of the basic compound existed in the reaction solution is preferably 1 equivalent or greater, and more preferably 1.5 equivalents or greater, with respect to 1 equivalent (eq.) of the ketone derivative (II) from the perspective of yield. Furthermore, from the perspective of yield, the amount of the basic compound is preferably 3 equivalents or less, and more preferably 2.2 equivalents or less, with respect to 1 equivalent (eq.) of the ketone derivative (II).

In one aspect of the present invention, in a case where acetone cyanohydrin is selected as the cyanide compound and the reaction is performed in coexistence with DIPEA as the basic compound in Step 1-1, the amount of DIPEA acting on the ketone derivative (II) is most preferably 2 equivalents (eq.) of DIPEA with respect to 1 equivalent (eq.) of the ketone derivative (II).

Step 1-2: Washing

In Step 1-2, the intermediate product (III) produced in Step 1-1 is washed with an alkaline aqueous solution. Specifically, toluene and an alkaline aqueous solution are added to the reaction solution after Step 1-1, and the reaction solution is separated. To the obtained organic layer, an alkaline aqueous solution is added, and the organic layer is washed.

Examples of the alkaline aqueous solution include a potassium hydroxide solution and a sodium hydroxide solution. From the perspective of liquid separability, a potassium hydroxide solution is preferred.

The amount of the alkaline aqueous solution used for the washing is only required to be an adequate amount that can remove major by-products from the organic layer obtained by adding toluene and the alkaline aqueous solution to the reaction solution after Step 1-1 to separate the solution.

In the production method 1 according to one aspect of the present invention, by performing Step 1-1 described above, yield is improved compared to those of known production methods. For example, Non-Patent Document 1 (James H. et al., Journal of Heterocyclic Chemistry, 21(3), 903-4; 1984) describes a similar reaction example using KCN, but the yield is 54%. On the other hand, as described in Examples below, by the production method 1 according to one aspect of the present invention, the yield is increased by 10% or greater compared to that of the method described in Non-Patent Document 1 (see Synthesis Example 1-1 to Synthesis Example 1-5 described in Examples below).

Furthermore, by the production method 1 according to one aspect of the present invention, by performing Step 1-2 described above, as described in Examples below, the purity of the obtained crude material is improved by approximately 10 mass % compared to the case where Step 1-2 described above is not performed (from the comparison between Synthesis Example 1-1 and Synthesis Example 1-2 or the comparison between Synthesis Example 1-4 and Synthesis Example 1-5 described in Examples below).

2. Method of Producing Compound Represented by General Formula (IV)-1

The method of producing a compound represented by General Formula (IV) according to one aspect of the present invention (hereinafter, referred to as "production method 2") will be described.

[Chem. 17]

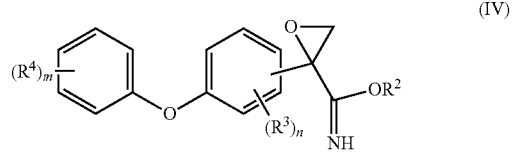

(IV)

In Formula (IV), $R^2$ is a $C_1$-$C_6$-alkyl group.

$R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group.

m is an integer from 0 to 5, and when m is 2 or greater, a plurality of $R^4$ moieties may be different from each other.

n is an integer from 0 to 4, and when n is 2 or greater, a plurality of $R^3$ moieties may be different from each other.

The compound represented by General Formula (IV) above is an intermediate product of the azole derivative (I) described above. $R^3$, $R^4$, m, and n in General Formula (IV) above are respectively identical to $R^3$, $R^4$, m, and n in Formula (I) above. For convenience of explanation, the compound represented by General Formula (IV) is referred to as "intermediate product (IV)".

The production method 2 according to one aspect of the present invention includes: producing a compound represented by General Formula (IV) above by allowing an alkoxide compound having from 1 to 6 carbons to act on a compound represented by General Formula (III) (Step 2-1).

The production method 2 according to one aspect of the present invention produces an intermediate product (IV) from the intermediate product (III) according to Scheme 2 below. Note that $R^2$, $R^3$, $R^4$, m, and n in the scheme below respectively correspond to $R^2$, $R^3$, $R^4$, m, and n in General Formula (IV) above.

Scheme 2

[Chem. 18]

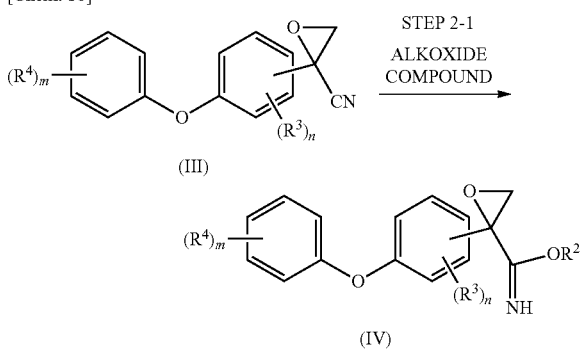

Step 2-1: Production of Intermediate Product (IV)

In the production method 2 according to one aspect of the present invention, in Step 2-1, the intermediate product (IV) is produced by allowing an alkoxide compound having from 1 to 6 carbons to act on the intermediate product (III) in a freely chosen organic solvent (e.g., methanol or toluene). The reaction conditions of Step 2-1 is not particularly limited and can be appropriately set.

Since the intermediate product (III) produced by the production method 1 according to one aspect of the present invention has a high purity, the intermediate product (III) used in Step 2-1 is preferably the intermediate product produced by the production method 1 according to one aspect of the present invention described above.

The alkoxide compound having from 1 to 6 carbons is preferably a metal alkoxide compound having from 1 to 6 carbons. The metal element constituting the metal alkoxide compound is not particularly limited. Examples of the alkoxide compound having from 1 to 6 carbons include sodium methoxide, potassium methoxide, and sodium ethoxide. From the perspective of yield, a solution of sodium methoxide in methanol is preferably used.

In Step 2-1, the amount of the alkoxide compound having from 1 to 6 carbons acting on the intermediate product (III) is preferably 1.6 equivalents or greater, and more preferably 2.2 equivalents or greater, with respect to 1 equivalent (eq.) of the intermediate product (III) from the perspective of performing the reaction without excess or deficiency. Furthermore, from the perspective of yield, the amount of the alkoxide compound having from 1 to 6 carbons acting on the intermediate product (III) is preferably 3 equivalents or less, and more preferably 2.4 equivalents or less, with respect to 1 equivalent (eq.) of the intermediate product (III).

3. Method of Producing Compound Represented by General Formula (V)-1

The method of producing a compound represented by General Formula (V) according to one aspect of the present invention (hereinafter, referred to as "production method 3") will be described.

[Chem. 19]

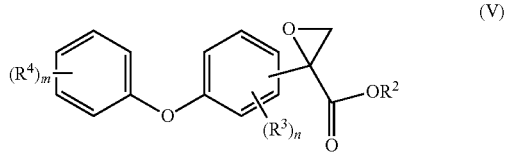

In Formula (V), $R^2$ is a $C_1$-$C_6$-alkyl group.

$R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group.

m is an integer from 0 to 5, and when m is 2 or greater, a plurality of $R^4$ moieties may be different from each other.

n is an integer from 0 to 4, and when n is 2 or greater, a plurality of $R^3$ moieties may be different from each other.

The compound represented by General Formula (V) above is an intermediate product of the azole derivative (I) described above. For convenience of explanation, the compound represented by General Formula (V) is referred to as "intermediate product (V)".

$R^2$, $R^3$, $R^4$, m, and n in General Formula (V) above are respectively identical to $R^3$, $R^4$, m, and n in Formula (I) above.

The production method 3 according to one aspect of the present invention includes: producing the compound represented by General Formula (IV) by allowing an alkoxide compound having from 1 to 6 carbons to act on a compound represented by General Formula (III) above (Step 3-1), and producing the compound represented by General Formula (V) above by allowing an acidic compound to act on the compound represented by General Formula (IV) above produced in the producing a compound represented by General Formula (IV) above (Step 3-2).

The production method 3 according to one aspect of the present invention produces an intermediate product (V) from the intermediate product (III) according to Scheme 3 below.

Note that $R^2$, $R^3$, $R^4$, m, and n in the scheme below respectively correspond to $R^2$, $R^3$, $R^4$, m, and n in General Formula (V) above.

Scheme 3

[Chem. 20]

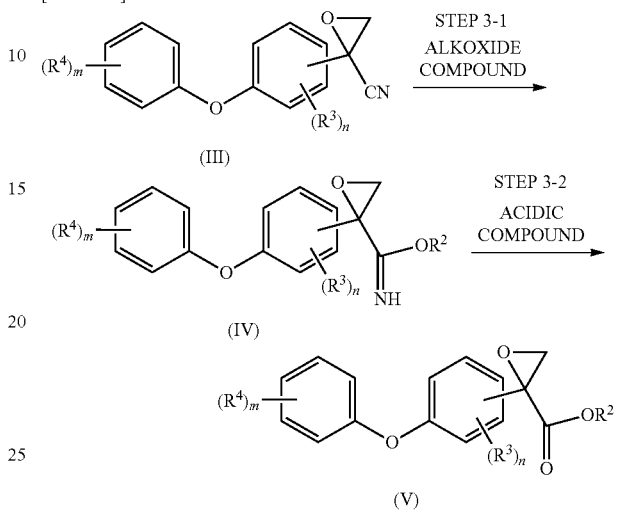

Step 3-1: Production of Intermediate Product (IV)

In the production method 3 according to one aspect of the present invention, in Step 3-1, the intermediate product (IV) is produced by allowing an alkoxide compound having from 1 to 6 carbons to act on the intermediate product (III) in a freely chosen organic solvent (e.g., methanol or toluene). The reaction conditions of Step 3-1 is not particularly limited and can be appropriately set. The types, amounts, and the like of the intermediate product (III) and the alkoxide compound having from 1 to 6 carbons used in Step 3-1 are as described in Step 2-1 above.

Step 3-2: Production of Intermediate Product (V)

In Step 3-2, the acidic compound is allowed to act on the intermediate product (IV) produced in Step 3-1 above in a freely chosen organic solvent (e.g., toluene), and thus an intermediate product (V) is produced. The reaction conditions of Step 3-2 is not particularly limited and can be appropriately set.

The intermediate product (IV) used in Step 3-2 may be present in the reaction solution obtained in Step 3-1 above, or may be isolated from the reaction solution obtained in Step 3-1 above and purified. Since the production process can be simplified by performing the reaction in one pot, as the intermediate product (IV) used in Step 3-2, the reaction solution obtained in Step 3-1 above is preferably used as is.

Examples of the acidic compound include a hydrochloric acid solution and a sulfuric acid solution. From the perspective of uniformity of the reaction solution, a sulfuric acid solution is preferred.

In Step 3-2, the amount of the acidic compound acting on the intermediate product (IV) is preferably 4 equivalents or greater, and more preferably 4.4 equivalents or greater, with respect to 1 equivalent (eq.) of the intermediate product (IV) from the perspective of performing the reaction without excess or deficiency. Furthermore, from the perspective of yield, the amount of the acidic compound acting on the intermediate product (IV) is preferably 5.0 equivalents or less, and more preferably 4.5 equivalents or less, with respect to 1 equivalent (eq.) of the intermediate product (IV).

In the production method 3 according to one aspect of the present invention, the intermediate product (V) can be produced at a lower cost than those of known production methods. For example, in the method (Synthesis Example 3) described in Patent Document 1 (WO 2019/093522), production cost is increased because expensive compounds, such as iodine and iodomethane, are used to produce the intermediate product (V). On the other hand, the production method 3 according to one aspect of the present invention makes it possible to suppress the production cost of the intermediate product (V) by using a raw material with a lower cost.

Furthermore, in the production method 3 according to one aspect of the present invention, yield is improved compared to those of known production methods. For example, in the method (Synthesis Example 3) described in Patent Document 1 (WO 2019/093522), yield of the intermediate product (V) is approximately 60%. Furthermore, Non-Patent Document 2 (Muller A. J. et al., Journal of Organic Chemistry, 47, 2342-2352; 1982) describes a similar reaction that converts a cyano group into an ester group, but the yield is 85%. On the other hand, as described in Examples below, in the production method 3 according to one aspect of the present invention, the yield is 92.0% and is significantly improved compared to those of the methods described in Patent Document 1 and Non-Patent Document 2 (see Synthesis Example 3-1 described in Examples below).

4. Method of Producing Compound Represented by General Formula (V)-2

The method of producing a compound represented by General Formula (V) according to another aspect of the present invention (hereinafter, referred to as "production method 4") will be described. The production method 4 according to one aspect of the present invention includes: producing the compound represented by General Formula (III) above by allowing a cyanide compound to act on a ketone derivative represented by General Formula (II) (Step 4-1), producing a compound represented by General Formula (IV) by allowing an alkoxide compound having from 1 to 6 carbons to act on a reaction solution after the producing the compound represented by General Formula (III) above (Step 4-2), and producing the compound represented by General Formula (V) above by allowing an acidic compound to act on a reaction solution after the producing the compound represented by General Formula (IV) above (Step 4-3).

The production method 4 according to one aspect of the present invention produces an intermediate product (V) from the ketone derivative (II) according to Scheme 4 below. Note that $R^2$, $R^3$, $R^4$, m, and n in the scheme below respectively correspond to $R^2$, $R^3$, $R^4$, m, and n in General Formula (V) above.

Scheme 4

[Chem. 21]

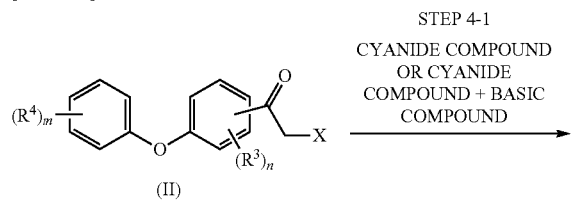

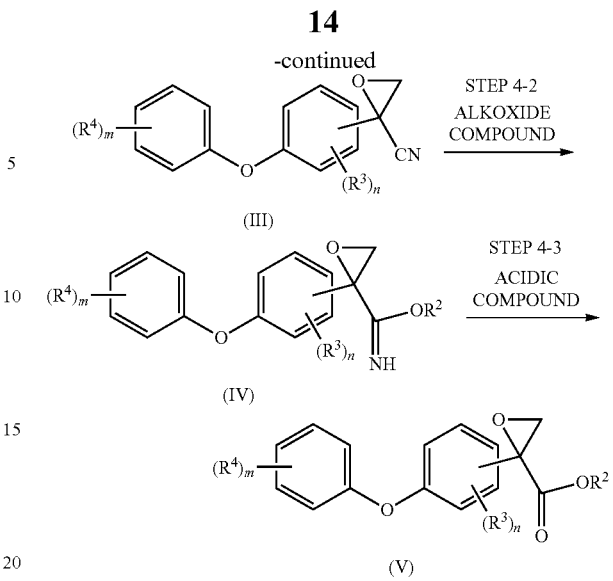

Step 4-1: Production of Intermediate Product (III)

In the production method 4 according to one aspect of the present invention, in Step 4-1, the intermediate product (III) is produced by allowing a cyanide compound to act on the ketone derivative (II) in an organic solvent that is suitable for progress of the reaction (e.g., methanol, ethanol, acetone, dimethylacetamide, toluene, and a mixed solvent of toluene and methanol; preferably methanol). The reaction conditions of Step 4-1, the types, amounts, and the like of the ketone derivative (II) and the cyanide compound used for the reaction are as described in Step 1-1 above.

Step 4-2: Production of Intermediate Product (IV)

In Step 4-2, the intermediate product (IV) is produced by allowing an alkoxide compound having from 1 to 6 carbons to act on the reaction solution after Step 4-1 above. The reaction conditions of Step 4-2 is not particularly limited and can be appropriately set. The type, amount, and the like of the alkoxide compound having from 1 to 6 carbons used for the reaction are as described in Step 2-1 above.

Step 4-3: Production of Intermediate Product (V)

In Step 4-3, the intermediate product (V) is produced by allowing an acidic compound to act on the reaction solution after Step 4-2 above. The type, amount, and the like of the acidic compound used for the reaction are as described in Step 3-2 above.

In the production method 4 according to one aspect of the present invention, the intermediate product (V) can be produced by performing the three steps, which are Step 4-1 to Step 4-3, in one pot without any post-treatment in the middle of steps after the intermediate product (II). Thus, in the production method 4 according to one aspect of the present invention, the process can be simplified.

5. Method of Producing Compound Represented by General Formula (IV)-2

The method of producing a compound represented by General Formula (IV) according to another aspect of the present invention (hereinafter, referred to as "production method 5") will be described. The production method 5 according to one aspect of the present invention includes: producing the compound represented by General Formula (III) above by allowing a cyanide compound to act on a ketone derivative represented by General Formula (II) (Step 5-1), and producing a compound represented by General Formula (IV) by allowing an alkoxide compound having from 1 to 6 carbons to act on a reaction solution after the producing the compound represented by General Formula (III) above (Step 5-2).

The production method 5 according to one aspect of the present invention produces an intermediate product (IV) from the ketone derivative (II) according to Scheme 5 below. Note that $R^2$, $R^3$, $R^4$, m, and n in the scheme below respectively correspond to $R^2$, $R^3$, $R^4$, m, and n in General Formula (IV) above.

Scheme 5

[Chem. 22]

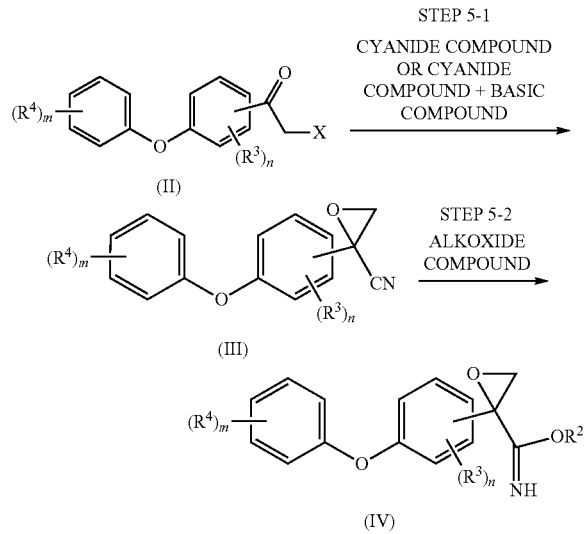

Step 5-1: Production of Intermediate Product (III)
In the production method 5 according to one aspect of the present invention, in Step 5-1, the intermediate product (III) is produced by allowing a cyanide compound to act on the ketone derivative (II) in an organic solvent that is suitable for progress of the reaction (e.g., methanol, ethanol, acetone, dimethylacetamide, toluene, and a mixed solvent of toluene and methanol; preferably methanol). The reaction conditions of Step 5-1, the types, amounts, and the like of the ketone derivative (II) and the cyanide compound used for the reaction are as described in Step 1-1 above.
Step 5-2: Production of Intermediate Product (IV)
In Step 5-2, the intermediate product (IV) is produced by allowing an alkoxide compound having from 1 to 6 carbons to act on the reaction solution after Step 5-1 above. The reaction conditions of Step 5-2 is not particularly limited and can be appropriately set. The type, amount, and the like of the alkoxide compound having from 1 to 6 carbons used for the reaction are as described in Step 2-1 above.

In the production method 5 according to one aspect of the present invention, the intermediate product (IV) can be produced by performing the two steps, which are Step 5-1 and Step 5-2, in one pot without any post-treatment in the middle of steps after the intermediate product (II). Thus, in the production method 5 according to one aspect of the present invention, the process can be simplified.

6. Compound Represented by General Formula (VI)
The compound represented by General Formula (VI) according to one aspect of the present invention will be described below.

[Chem. 23]

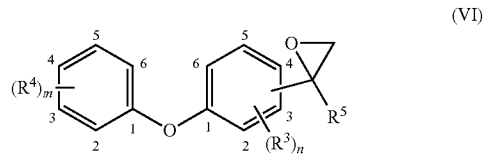

In Formula (VI), $R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;

m is an integer from 0 to 5, and when m is 2 or greater, a plurality of $R^4$ moieties may be different from each other;

n is an integer from 0 to 4, and when n is 2 or greater, a plurality of $R^3$ moieties may be different from each other;

$R^5$ is —CN or —CNHOR$^2$; and $R^2$ is a $C_1$-$C_6$-alkyl group.

$R^3$, $R^4$, m, and n in General Formula (VI) above are respectively identical to $R^3$, $R^4$, m, and n in Formula (I) above.

In the compound represented by General Formula (VI) according to one aspect of the present invention, in General Formula (VI) above, for example, m and n are 1, $R^5$ is —CN, a substitution position (*) of a functional group represented by Formula (VII) is at 4-position, $R^3$ is 3-Cl, and $R^4$ is 4-Cl. In other words, in the compound represented by General Formula (VI) according to one aspect of the present invention, in General Formula (VI) above, m and n are 1, $R^5$ is —CN, $R^3$ and $R^4$ are each —Cl, a substitution position (*) of a functional group represented by Formula (VII) is at 4-position of the phenoxyphenyl group, a substitution position of $R^3$ is at 3-position of the phenoxyphenyl group, and a substitution position of $R^4$ is at 4-position of the phenoxyphenyl group. The compound is an aspect of the intermediate product (III), which is an intermediate product of the azole derivative (I).

[Chem. 24]

Furthermore, in the compound represented by General Formula (VI) according to one aspect of the present invention, in General Formula (VI) above, m and n are 1, $R^5$ is —CNHOR$^2$, $R^2$ is a methyl group, a substitution position (*) of a functional group represented by Formula (VII) is at 4-position, $R^3$ is 3-Cl, and $R^4$ is 4-Cl. In other words, in the compound represented by General Formula (VI) according to one aspect of the present invention, in General Formula (VI) above, m and n are 1, $R^5$ is —CNHOR$^2$, $R^2$ is a methyl group, $R^3$ and $R^4$ are each —Cl, a substitution position (*) of a functional group represented by Formula (VII) is at 4-position of the phenoxyphenyl group, a substitution position of $R^3$ is at 3-position of the phenoxyphenyl group, and a substitution position of $R^4$ is at 4-position of the phenoxyphenyl group. The compound is an aspect of the intermediate product (IV), which is an intermediate product of the azole derivative (I).

[Chem. 25]

(VII)

The intermediate product (III) and the intermediate product (IV) can be produced respectively by the production method 1 and the production method 2 described above.

(Additional Matters)

The present invention is not limited to the above-described embodiments, and various modifications can be made within the scope of the claims, and embodiments obtained by appropriately combining technical means disclosed in different embodiments are also included in the technical scope of the present invention.

SUMMARY

The production method according to a first aspect of the present invention is a method of producing a compound represented by General Formula (III), the method including: producing the compound represented by General Formula (III) above by allowing a cyanide compound to act on a ketone derivative represented by General Formula (II); and washing the compound represented by General Formula (III) above produced in the producing the compound represented by General Formula (III) above with an alkaline aqueous solution.

The production method according to a second aspect of the present invention is a method of producing a compound represented by General Formula (IV), the method including: producing the compound represented by General Formula (IV) above by allowing an alkoxide compound having from 1 to 6 carbons to act on a compound represented by General Formula (III).

The production method according to a third aspect of the present invention is a method of producing a compound represented by General Formula (V), the method including: producing a compound represented by General Formula (IV) by allowing an alkoxide compound having from 1 to 6 carbons to act on a compound represented by General Formula (III), and producing the compound represented by General Formula (V) above by allowing an acidic compound to act on the compound represented by General Formula (IV) above produced in the producing a compound represented by General Formula (IV) above.

In the production method according to a fourth aspect of the present invention, the compound represented by General Formula (III) above in the second aspect may be produced by the production method according to the first aspect.

In the production method according to a fifth aspect of the present invention, the compound represented by General Formula (III) above in the third aspect may be produced by the production method according to the first aspect.

The production method according to a sixth aspect of the present invention is a method of producing a compound represented by General Formula (V), the method including: producing a compound represented by General Formula (III) by allowing a cyanide compound to act on a ketone derivative represented by General Formula (II), producing a compound represented by General Formula (IV) by allowing an alkoxide compound having from 1 to 6 carbons to act on a reaction solution after the producing a compound represented by General Formula (III) above, and producing the compound represented by General Formula (V) above by allowing an acidic compound to act on a reaction solution after the producing a compound represented by General Formula (IV) above.

In the production method according to a seventh aspect of the present invention, the cyanide compound in the first aspect may be potassium cyanide, sodium cyanide, or acetone cyanohydrin, and in a case where acetone cyanohydrin is selected as the cyanide compound, the producing a compound represented by General Formula (III) above may be performed in coexistence with a basic compound.

In the production method according to an eighth aspect of the present invention, the cyanide compound in the sixth aspect may be potassium cyanide, sodium cyanide, or acetone cyanohydrin, and in a case where acetone cyanohydrin is selected as the cyanide compound, the producing a compound represented by General Formula (III) above may be performed in coexistence with a basic compound.

The compound according to a ninth aspect of the present invention is a compound represented by General Formula (VI) below.

In the compound according to a tenth aspect of the present invention, in General Formula (VI) above in the ninth aspect, m and n may be 1, $R^5$ may be —CN, a substitution position (*) of a functional group represented by Formula (VII) may be at 4-position, $R^3$ may be 3-Cl, and $R^4$ may be 4-Cl.

In the compound according to an eleventh aspect of the present invention, in General Formula (VI) above in the ninth aspect, m and n may be 1, $R^5$ may be —CNHOR², $R^2$ may be a methyl group, a substitution position (*) of a functional group represented by Formula (VII) may be at 4-position, $R^3$ may be 3-Cl, and $R^4$ may be 4-Cl.

EXAMPLES

An example of the present invention will be described below.

The present invention will now be explained in greater detail through the use of examples. Moreover, the present invention is not limited to the examples given below, as long as the gist of the present invention is not exceeded.

Example 1

Synthesis Example 1-1

Synthesis of 2-(2-chloro-4-(4-chlorophenoxy)phenyl)oxirane-2-carbonitrile (Intermediate Product (III))

KCN, Br Raw Material, Alkaline Washing Included
The title compound was produced according to the following Scheme A.

Scheme A

[Chem. 26]

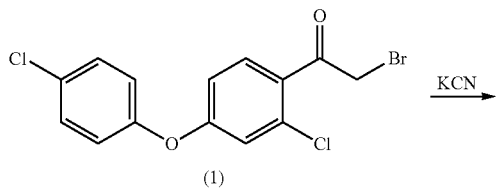

(1)

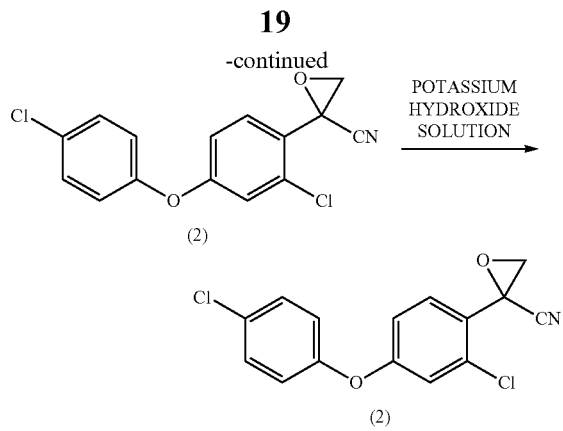

In a raw 2-bromo-1-(2-chloro-4-(4-chlorophenoxy)phenyl)ethan-1-one (compound represented by Formula (1) in Scheme A above) (3.89 g, purity: 82.92 wt %, net content: 3.23 g), methanol (17.9 mL) and potassium cyanide (0.758 g, 1.3 eq.) were added and agitated for 2.5 hours.

In the reaction solution, toluene (30 mL) and a 2 mol/L potassium hydroxide solution (20 mL) were added, and the solution was separated. Re-extraction from the aqueous layer was performed twice by using toluene (30 mL). The obtained organic layers were combined and successively washed with a 2 mol/L potassium hydroxide solution (20 mL), a saturated ammonium chloride solution (20 mL), and a saturated salt solution (20 mL), dried with sodium sulfate, and concentrated under reduced pressure, and thus a residue (2.91 g) was obtained as a yellow oily substance.

HPLC quantification of this residue was performed. As a result, for the title compound (compound represented by Formula (2) in Scheme A above), the yield was 76.5%, and the purity was 72.0 wt %.

Example 2

Synthesis Example 1-2

Synthesis of 2-(2-chloro-4-(4-chlorophenoxy)phenyl)oxirane-2-carbonitrile (Intermediate Product (III))

KCN, Br Raw Material, Alkaline Washing Not Included
The title compound was produced according to the following Scheme B.

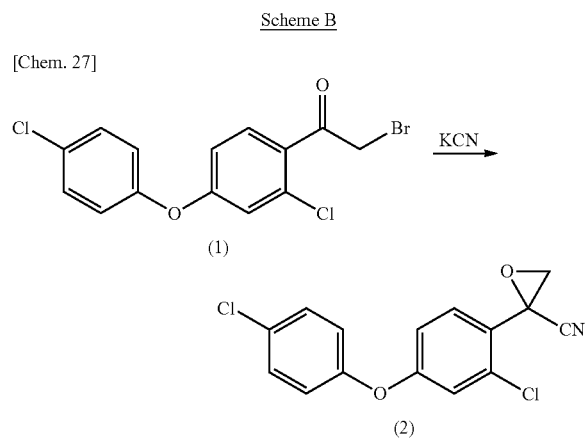

A raw 2-bromo-1-(2-chloro-4-(4-chlorophenoxy)phenyl)ethan-1-one (compound represented by Formula (1) in Scheme B above) (3.94 g, purity: 82.92 wt %, net content: 3.27 g) was dissolved in methanol (18.1 mL, 2 L/mol), and potassium cyanide (0.768 g, 1.3 eq.) was added at room temperature and agitated for 3 hours.

The methanol was distilled off from the reaction solution under reduced pressure, and water (20 mL) was added to the residue, and extraction was performed twice by using ethyl acetate (20 mL). The obtained organic layers were combined and washed with a saturated salt solution (20 mL), dried with sodium sulfate, and concentrated under reduced pressure, and thus a residue (3.58 g) was obtained as a brown oily substance.

HPLC quantification of this residue was performed. As a result, for the title compound (compound represented by Formula (2) in Scheme B above), the yield was 77.9%, and the purity was 60.5 wt %.

Example 3

Synthesis Example 1-3

Synthesis of 2-(2-chloro-4-(4-chlorophenoxy)phenyl)oxirane-2-carbonitrile (Intermediate Product (III))

KCN, Cl Raw Material, Isolated
The title compound was produced according to the following Scheme C.

Scheme C

[Chem. 28]

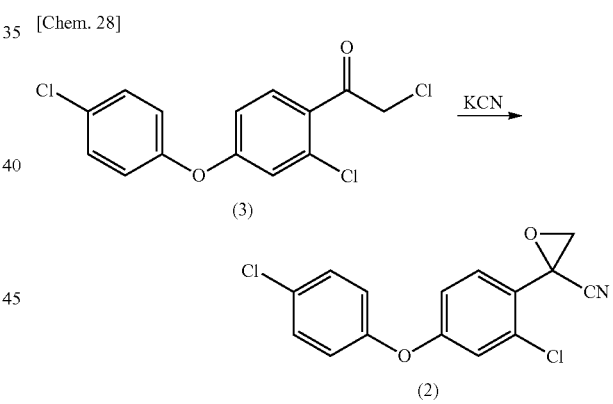

A purified 2-chloro-1-(2-chloro-4-(4-chlorophenoxy)phenyl)ethan-1-one (compound represented by Formula (3) in Scheme C above) (285.5 mg) was dissolved in methanol (1.8 mL, 2 L/mol), and potassium cyanide (59 mg, 1 eq.) was added at room temperature, agitated for 8 hours, and then allowed to stand still for 2 days.

The methanol was distilled off from the reaction solution under reduced pressure, and water (10 mL) was added to the residue, and extraction was performed three times by using toluene (10 mL). The obtained organic layers were combined and washed with a saturated salt solution (10 mL), dried with sodium sulfate, and concentrated under reduced pressure. The residue (271.7 mg) was purified using Sep-Pak Vac 35 cc (10 g) Silica Cartridge, available from Waters Corporation, with a developer (hexane:ethyl acetate=50:1) and a developer (hexane:ethyl acetate=20:1) successively, and thus the title compound (compound represented by Formula (2) in Scheme C above) (177.8 mg) was obtained as a colorless, transparent oily substance (isolated yield: 64.2%).

$^1$H-NMR (400 MHz, CDCl$_3$) δ: 7.42 (d, J=8.6 Hz, 1H), 7.36 (d, J=9.0 Hz, 2H), 7.03 (d, J=2.4 Hz, 1H), 6.99 (d, J=9.0 Hz, 2H), 6.91 (dd, J=8.6, 2.4 Hz, 1H), 3.60 (d, J=5.8 Hz, 1H), 3.05 (d, J=5.8 Hz, 1H).

Example 4

Synthesis Example 1-4

Synthesis of 2-(2-chloro-4-(4-chlorophenoxy)phenyl)oxirane-2-carbonitrile (Intermediate Product (III))

ACH/K$_2$CO$_3$, Br Raw Material, Alkaline Washing Not Included

The title compound was produced according to the following Scheme D.

Scheme D

[Chem. 29]

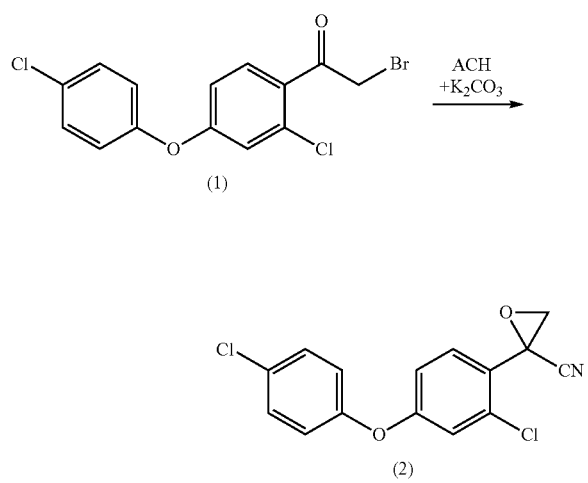

A purified 2-bromo-1-(2-chloro-4-(4-chlorophenoxy)phenyl)ethan-1-one (compound represented by Formula (1) in Scheme D above) (180.0 mg) was added in methanol (0.5 mL, 1 L/mol) and cooled in ice.

Then, acetone cyanohydrin (50.6 µL=0.553 mmol, 1.1 eq.) and potassium carbonate (76.5 mg, 1.1 eq.) were added and agitated for 2.5 hours.

The reaction solution was subjected to extraction three times by using ethyl acetate (5 mL). The obtained organic layers were combined and washed with a saturated salt solution (10 mL), dried with sodium sulfate, and concentrated under reduced pressure, and thus a residue (157.3 mg) was obtained as a pale yellow oily substance.

HPLC quantification of this residue was performed. As a result, for the title compound (compound represented by Formula (2) in Scheme D above), the yield was 65.4%, and the purity was 73.3 wt %.

Example 5

Synthesis Example 1-5

Synthesis of 2-(2-chloro-4-(4-chlorophenoxy)phenyl)oxirane-2-carbonitrile (intermediate product (III))

ACH/DIPEA, Br Raw Material, Alkaline Washing Included

The title compound was produced according to the following Scheme E.

Scheme E

[Chem. 30]

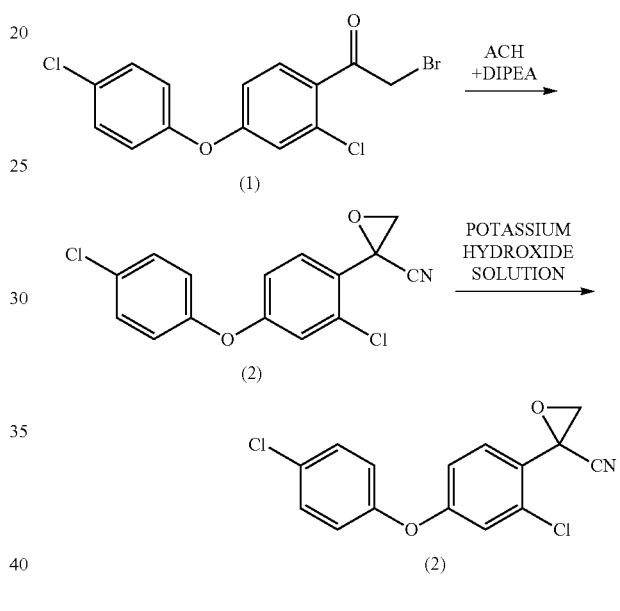

In a raw 2-bromo-1-(2-chloro-4-(4-chlorophenoxy)phenyl)ethan-1-one (compound represented by Formula (1) in Scheme E above) (4.36 g, purity: 82.92 wt %, net content: 3.62 g), 10 mL of methanol was added and agitated while being cooled in ice water.

Then, 1.70 g of acetone cyanohydrin (purity: 96%, 19.18 mmol, 1.92 eq.) and 2.84 g of N-ethyldiisopropylamine (DIPEA) (purity: 97%, 21.31 mmol, 2.13 eq.) were successively added and agitated for 5 hours while being cooled in ice water.

To the reaction solution, 20 mL of toluene and 10 mL of a 6.6 wt % potassium hydroxide solution were added and partitioned. The bottom layer was further partitioned by using 10 mL of toluene. The obtained organic layers were combined and successively washed with a 6.6 wt % potassium hydroxide solution (5 mL) and a saturated salt solution (10 mL), dried with sodium sulfate, and concentrated under reduced pressure, and thus a residue (2.80 g) was obtained as a reddish brown candy-like material.

HPLC quantification of this residue was performed. As a result, for the title compound (compound represented by Formula (2) in Scheme E above), the yield was 74.4%, and the purity was 81.8 wt %.

23
Example 6

Synthesis Example 2-1

Synthesis of methyl 2-(2-chloro-4-(4-chlorophenoxy)phenyl)oxiran-2-carboimidate (Intermediate Product (IV))

Isolated

The title compound was produced according to the following Scheme F.

Scheme F

[Chem. 31]

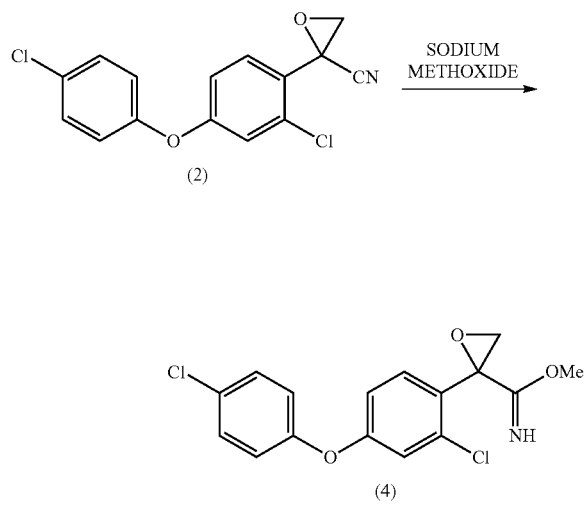

A purified 2-(2-chloro-4-(4-chlorophenoxy)phenyl)oxiran-2-carbonitrile (compound represented by Formula (2) in Scheme F above) (721 mg) was dissolved in methanol (4.7 mL), sodium methoxide (153 mg, 1.2 eq.) was added at room temperature and agitated for 1 hour.

The methanol was distilled off from the reaction solution under reduced pressure, and a saturated sodium bicarbonate solution (20 mL) and ethyl acetate (20 mL) were added to the residue, and the organic layer was separated. The aqueous layer was subjected to extraction twice by using ethyl acetate (20 mL). The obtained organic layers were combined and washed with a saturated salt solution (20 mL), dried with sodium sulfate, and concentrated under reduced pressure. The residue (858 mg) was purified by silica gel column chromatography (Kanto Chemical 60 N (spherical, neutral), 50 g, hexane:ethyl acetate=4:1), and the title compound (compound represented by Formula (4) in Scheme F above) (666 mg) was obtained as a colorless, transparent oily substance. The isolated yield of the title compound was 83.7%. $^1$H-NMR (400 MHz, CDCl$_3$) δ: 7.63 (br.s, 1H), 7.34 (d, J=8.8 Hz, 2H), 7.33 (d, J=2.4 Hz, 1H), 7.00 (d, J=8.8 Hz, 1H), 6.99 (d, J=8.8 Hz, 2H), 6.88 (dd, J=8.8, 2.4 Hz, 1H), 3.77 (s, 3H), 3.28 (d, J=5.7 Hz, 1H), 3.14 (d, J=5.7 Hz, 1H).

24
Example 7

Synthesis Example 3-1

Synthesis of methyl 2-(2-chloro-4-(4-chlorophenoxy)phenyl)oxiran carboxylate (Intermediate Product (V))

The title compound was produced according to the following Scheme G.

Scheme G

[Chem. 32]

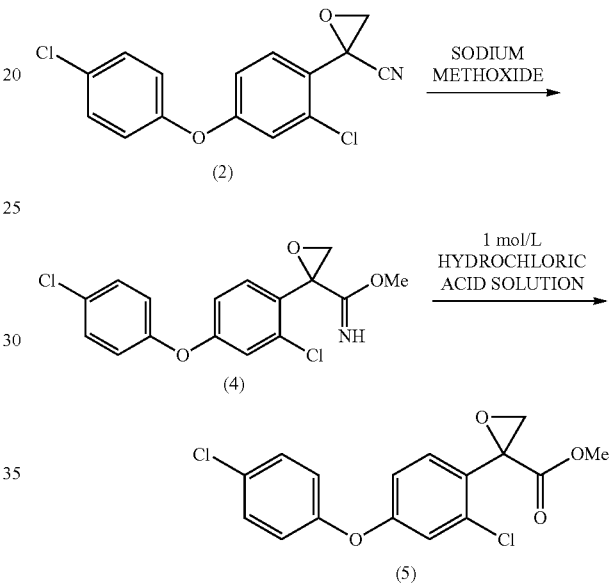

In a raw 2-(2-chloro-4-(4-chlorophenoxy)phenyl)oxiran-2-carbonitrile (compound represented by Formula (2) in Scheme G above) (34.40 g, purity: 63.78 wt %, net content: 21.94 g), methanol (143 mL) and toluene (72 mL) were added and cooled in ice.

Then, a 28 wt % sodium methoxide/methanol solution (30.4 g, 2.2 eq.) was added dropwise over 20 minutes, and then the mixture was agitated for 2 hours.

Subsequently, toluene (71 mL) was added, a 1 mol/L hydrochloric acid solution (315 mL=315 mmol, 4.4 eq.) was added, ice water bath was removed, and the mixture was agitated for 2 hours.

The reaction solution was separated, and the aqueous layer was subjected to re-extraction by using toluene (143 mL). The obtained organic layers were combined and successively washed with a saturated sodium bicarbonate solution (143 mL) and a saturated salt solution (143 mL), dried with sodium sulfate, and concentrated under reduced pressure, and thus a residue (39.20 g) was obtained as a yellow oily substance.

HPLC quantification of this residue was performed. As a result, for the title compound (compound represented by Formula (5) in Scheme G above), the yield was 92.0%, and the purity was 57.0 wt %.

Example 8

Synthesis Example 4-1

Synthesis of methyl 2-(2-chloro-4-(4-chlorophenoxy)phenyl)oxiran-2-carboxylate (Intermediate Product (V))

The title compound was produced according to the following Scheme H.

Scheme H

[Chem. 33]

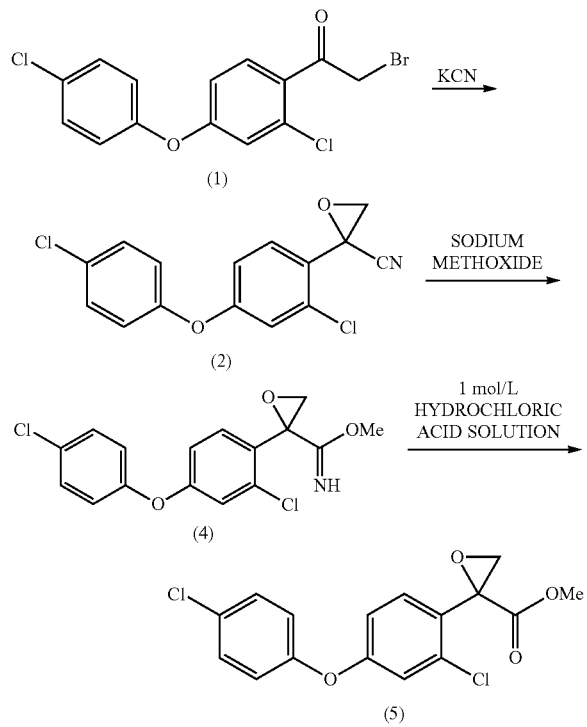

A raw 2-bromo-1-(2-chloro-4-(4-chlorophenoxy)phenyl)ethan-1-one (compound represented by Formula (1) in Scheme H above) (3.87 g, 82.92 wt %, net content: 3.21 g) was dissolved in methanol (17.8 mL), and potassium cyanide (0.755 g, 1.3 eq.) was added at room temperature and agitated for 5 hours.

Subsequently, a 28 wt % sodium methoxide/methanol solution (2.92 g, 1.7 eq.) was added and agitated for 3 hours, and then a 28 wt % sodium methoxide/methanol solution (1.72 g, 1.0 eq.) was further added and agitated for 1 hour.

Then, toluene (17.8 mL, 2 L/mol) and a 1 mol/L hydrochloric acid solution (38.3 mL=38.3 mmol, 4.3 eq.) were added and agitated for 1 hour.

Extraction from the reaction solution was performed three times by using toluene (30 mL). The obtained organic layers were combined and successively washed with a saturated sodium bicarbonate solution (30 mL) and a saturated salt solution (30 mL), dried with sodium sulfate, and concentrated under reduced pressure, and thus a residue (3.58 g) was obtained as a brown oily substance.

HPLC quantification of this residue was performed. As a result, for the title compound (compound represented by Formula (5) in Scheme H above), the yield was 53.9%, and the purity was 45.7 wt %.

INDUSTRIAL APPLICABILITY

An embodiment of the present invention can be utilized as an intermediate product for synthesizing an azole derivative useful as an agricultural or horticultural chemical.

The invention claimed is:

1. A method of producing a compound represented by General Formula (III),

[Chem. 1]

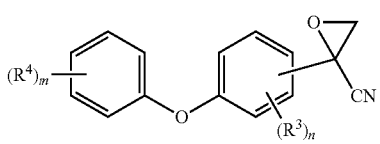

where $R^3$ and $R^4$ are each independently hydrogen, halogen, a $C_1$-$C_6$-alkyl group, a $C_1$-$C_6$-alkoxy group, a $C_1$-$C_6$-haloalkyl group, or a $C_1$-$C_6$-haloalkoxy group;

m is an integer from 0 to 5, and when m is 2 or greater, a plurality of $R^4$ moieties may be different from each other; and n is an integer from 0 to 4, and when n is 2 or greater, a plurality of $R^3$ moieties may be different from each other;

the method comprising:

producing the compound represented by General Formula (III) by allowing a cyanide compound to act on a ketone derivative represented by General Formula (II), and washing the compound represented by General Formula (III) produced in the producing the compound represented by General Formula (III) with an alkaline aqueous solution;

[Chem. 2]

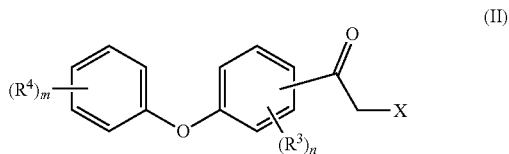

where X is a halogen atom, and $R^3$, $R^4$, m, and n in Formula (II) are respectively identical to $R^3$, $R^4$, m, and n in Formula (III).

2. The production method according to claim 1, wherein the cyanide compound is potassium cyanide, sodium cyanide, or acetone cyanohydrin, and in a case where acetone cyanohydrin is selected as the cyanide compound, the producing a compound represented by General Formula (III) is performed in coexistence with a basic compound.

* * * * *